United States Patent [19]

Keller

[11] Patent Number: 4,970,344

[45] Date of Patent: Nov. 13, 1990

[54] REACTIVATION OF SPENT ALKANOLAMINE

[75] Inventor: Alfred E. Keller, Ponca City, Okla.

[73] Assignee: Conoco Inc., Ponca City, Okla.

[21] Appl. No.: 69,124

[22] Filed: Jul. 2, 1987

[51] Int. Cl.$^5$ .................... C07C 209/84; C02F 1/42; C01B 31/20; B01D 15/04

[52] U.S. Cl. ................... 564/497; 210/669; 210/685; 423/228; 423/229

[58] Field of Search ........................................ 664/497

[56] References Cited

U.S. PATENT DOCUMENTS

| | | | |
|---|---|---|---|
| 2,797,188 | 6/1957 | Taylor et al. | 196/32 |
| 3,428,684 | 2/1969 | Tindall | 260/584 |
| 3,546,298 | 12/1970 | Tindall | 260/584 |
| 4,113,849 | 9/1978 | Atwood | 423/574 R |
| 4,180,655 | 12/1979 | Suami et al. | 536/17 R |
| 4,477,419 | 10/1984 | Pearce et al. | 423/228 |

Primary Examiner—Glennon H. Hollrah
Assistant Examiner—O'Sullivan, Peter G.
Attorney, Agent, or Firm—C. R. Schupbach

[57] ABSTRACT

Aqueous alkanolamine solution containing alkali metal salts of anions which form heat stable salts with such alkanolamine is reactivated by contacting the solution sequentially with a basic anion exchange resin to remove such anions and an acidic cation ion exchange resin to remove alkali metal ions.

20 Claims, 3 Drawing Sheets

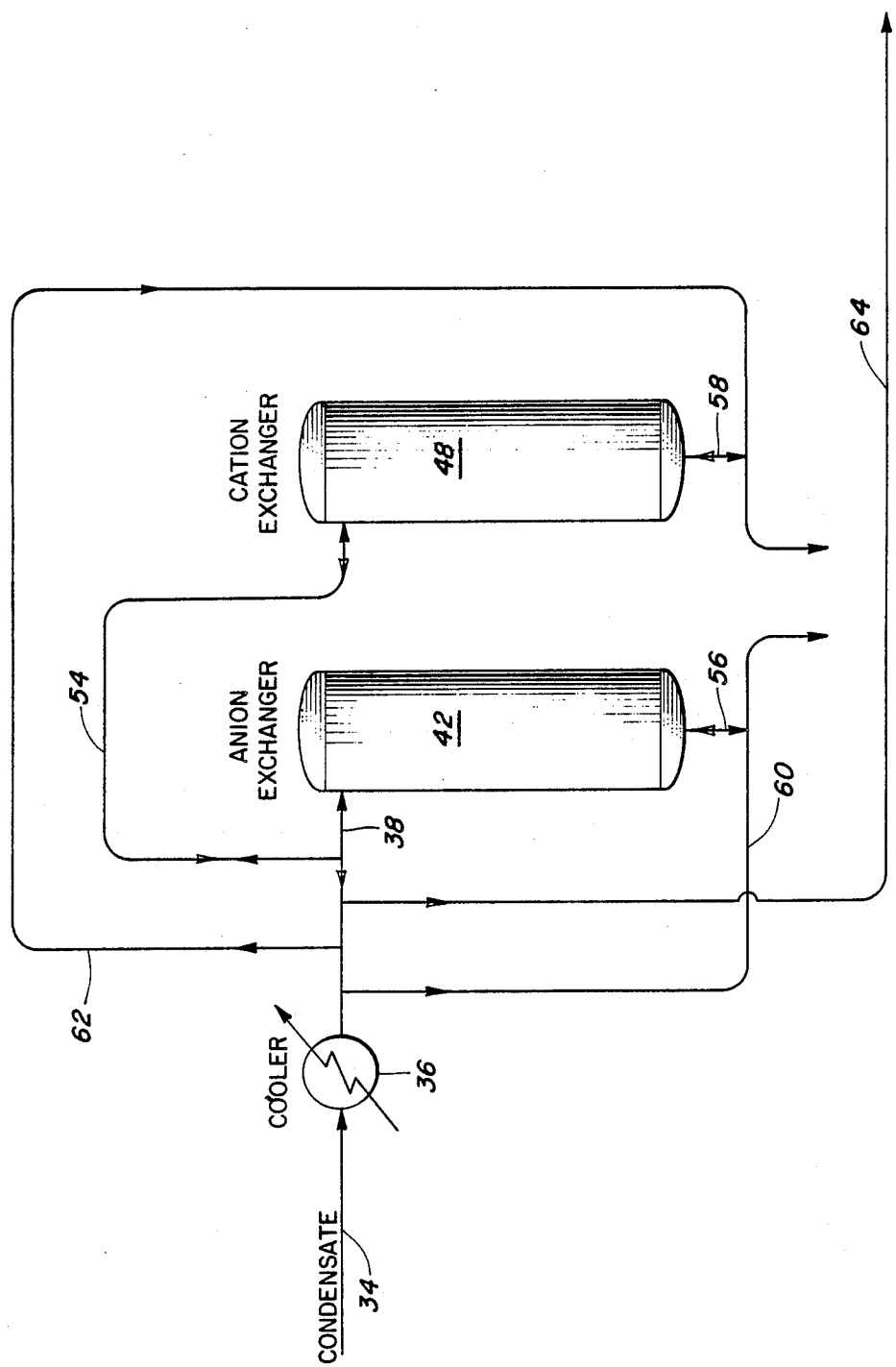

REACTIVATION OF SPENT ALKANOLAMINE

BACKGROUND AND SUMMARY OF THE INVENTION

Alkanolamine sweetening units are used for the removal of $H_2S$ and $CO_2$ from natural gases, enhanced oil recovery gases, refinery hydrodesulfurizer recycle gases, FCCU and Coker gas plant tail gases, LPG streams, and Claus sulfur recovery tail gases. The alkanolamines commonly used are ethanolamine, diethanolamine, methyl diethanolamine, diisopropanol amine, and triethanol amine. These compounds are weak bases in water solution. When solutions of alkanolamines are contacted in packed, sieve plate, bubble cap, or valve tray columns with streams containing $H_2S$ and $CO_2$, the $H_2S$ and $CO_2$ dissolve into the alkanolamine solution. The following chemical reactions then take place:

$H_2S$: $H_2S + A$ Amine $=$ AAmine $H^+ + HS^-$
$CO_2$: $H_2O + CO_2 + A$ Amine $=$ AAmine $H^+ + HCO_3^-$
General Eqn.: Acid Gases + Alkanolamine = Alkanolamine Salts of Acid Gases The solution of water, unreacted alkanolamine, and alkanolamine salts are subjected to steam stripping to decompose the alkanolamine salts and remove $H_2S$ and $CO_2$ from the alkanolamine. The $H_2S$ and $CO_2$ removed from the alkanolamine can then be processed by Claus sulfur recovery, incineration, fertilizer manufacture, or other means.

$H_2S$ and $CO_2$ are not the only gases in the above referred to streams which form weak acids when dissolved in water. Other such acid gases, as they are commonly called, that may appear in gas streams treated with alkanolamine include $SO_2$, COS, or HCN. These gases also undergo the same reactions as $H_2S$ and $CO_2$ to form alkanolamine salts. These salts, though, cannot be removed by steam stripping as $H_2S$ and $CO_2$ salts are. Thus, they remain and accumulate in the system.

Another problem is presented if oxygen gets into the alkanolamine system. Oxidation of acid gas conjugate base anions leads to the formation of other alkanolamine salts, most commonly salts of thiosulfate ($S_2O_3^{-2}$), sulfate ($SO_4^{-2}$), thiocyanate ($SCN^-$), or chloride ($Cl^-$). These salts cannot be regenerated by steam stripping either.

Alkanolamine salts which cannot be heat regenerated, called heat stable salts, reduce the effectiveness of alkanolamine treating. The alkanolamine is protonated and cannot react with either $H_2S$ or $CO_2$ which dissolve into the solution. Also, accumulated alkanolamine salts are known to cause corrosion in carbon steel equipment which is normally used in amine systems. The salts are also known to cause foaming problems which further decreases treating capacity.

The normal procedure used to deprotonate the alkanolamine, so it can react with $H_2S$ and $CO_2$, is to add an alkali metal hydroxide, such as NaOH, to the amine solution. The deprotonated alkanolamine then can be returned to $H_2S$ and $CO_2$ removal service. However, the sodium salts of the anions of the heat stable salts are also heat stable, are difficult to remove and thus accumulate in the alkanolamine solution, with attendant corrosion and foaming problems.

According to this invention the alkanolamine solution containing alkali metal salts of anions which form heat stable salts with such alkanolamine is contacted with a basic anion exchange resin to remove the heat stable anions from the solution and thereafter the solution is contacted with an acidic cation exchange resin whereby alkali metal ions are removed from the solution. In one aspect of the invention anions of heat stable salts of the alkanol amine are also removed by the basic anion exchange resin.

PRIOR ART

U. S. Pat. No. 2,797,188 discloses a system for regenerating spent alkanolamine absorbent used in treating petroleum hydrocarbon fluids. The regeneration is accomplished by contacting the spent alkanolamine absorbent containing heat stable alkanolamine salts such as those of thiocyanate and formic acid with a strongly basic anion exchange resin. The process removes the thiocyanate and formate ions in the alkanolamine solution with hydroxyl ions from the resin. The patent also reveals recharging of the resin by eluting with a sodium hydroxide stream to replace the heat stable anions again with hydroxyl ions. The patent also discloses flushing the resin with water prior to and subsequent to the elution with the sodium hydroxide stream.

U. S. Pat. No. 4,477,419 discloses the removal of $CO_2$ from gases with monoethanolamine absorbent. It also teaches the use of strongly basic anion exchange resin to remove anions of heat stable salts present in the alkanolamine solution.

BRIEF DESCRIPTION OF THE DRAWINGS

FIG. 3 is a schematic flow diagram showing the water wash sequence used during regeneration of the anion and cation exchange resins.

DETAILED DESCRIPTION OF THE INVENTION

The process of the invention may be used to reactivate any spent aqueous alkanolamine solution which contains alkali metal salts of anions which form heat stable salts with alkanolamines. As previously pointed out, such spent alkanolamine solutions result usually from processes in which hydrocarbon gases are contacted with an aqueous alkanolamine solution to absorb such impurities as $H_2S$ and $CO_2$ The resulting solutions which contain alkanolamine salts of $H_2S$ and $CO_2$ also contain salts of various inorganic acidic anions which are present in the hydrocarbon gases, or are formed in the solution by oxidation resulting from oxygen entering the alkanolamine treating system. In addition to the inorganic acid anions, the alkanolamine solution may also be contaminated with organic anions such as anions of formic and acetic acid and the like. The alkanolamine salts of $H_2S$ and $CO_2$ are not heat stable and may readily be decomposed by steam stripping with the concomitant removal of the released $H_2S$ and $CO_2$ The salts of the acid anions are unaffected by heat or steam stripping but may be converted from alkanolamine salts to alkali metal salts by introducing an alkali metal hydroxide to the alkanolamine solution. Any alkali metal hydroxide may be used for this purpose such as potassium hydroxide or lithium hydroxide, however, for economic reasons sodium hydroxide is preferred.

The process of this invention in which the alkali metal salts are removed to prevent buildup of these contaminants in the alkanolamine treating solution is best described by reference to the drawings.

Figure 1:
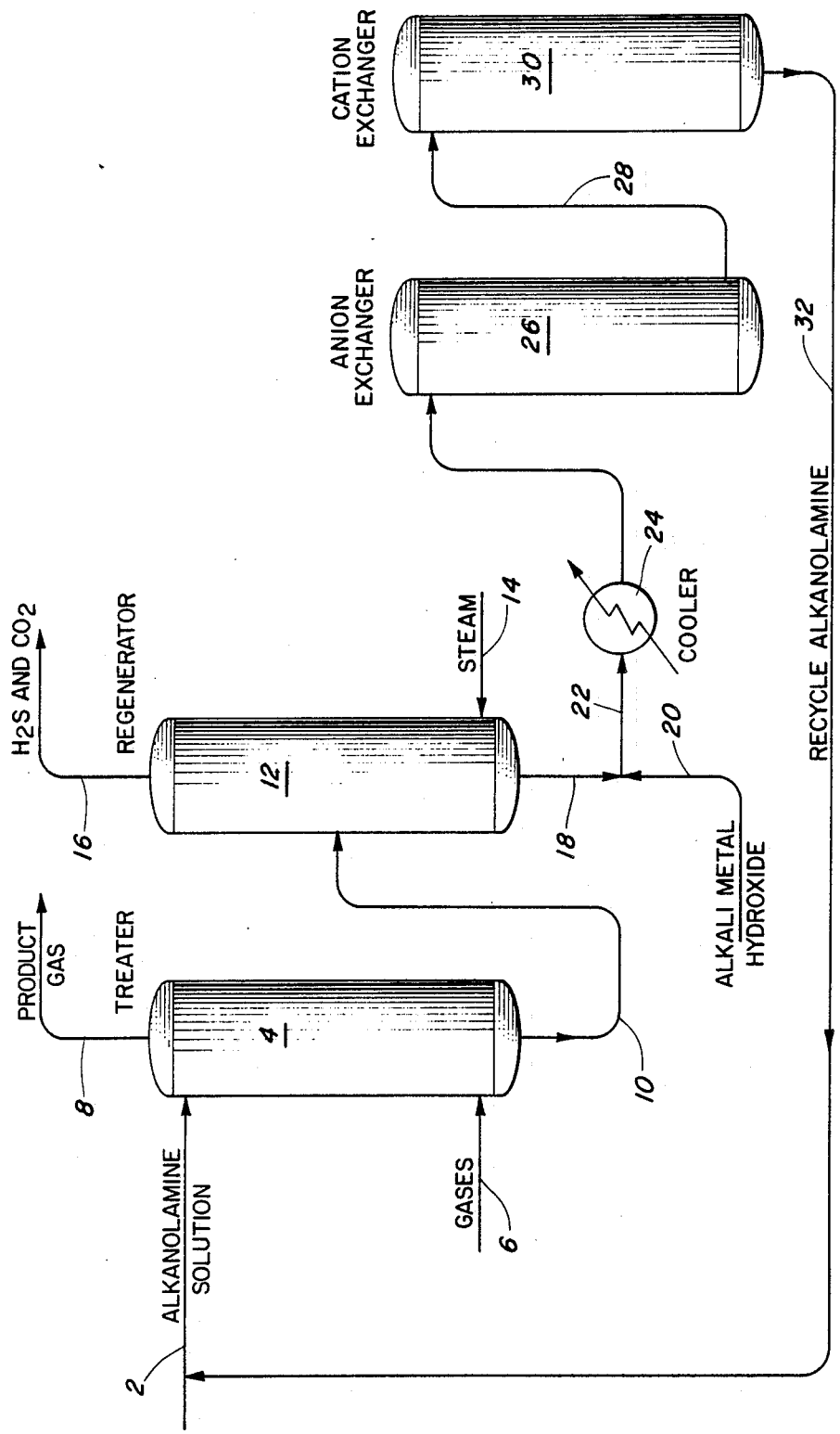
FIG. 1 is a schematic flow diagram which illustrates one embodiment of the invention.

Referring to FIG. 1, a gas containing undesirable hydrogen sulfide and carbon dioxide is introduced to a countercurrent treating zone 4 through line 6. The gas flows upwardly through treater 4 and contacts downflowing alkanolamine, in this instance, ethanolamine solution which is introduced to the top of the treater through line 2. The temperature in the treater is usually maintained in the range of between about 90 and about 130° F. while the pressure varies from between about 0 and about 1700 psig.

A product gas substantially free from hydrogen sulfide and carbon dioxide is withdrawn from the top of the treater via line 8. Ethanolamine solution containing absorbed hydrogen sulfide and carbon dioxide as salts of ethanolamine is removed from the treater through line 10 and introduced to regenerator 12. Steam introduced to the bottom of the regenerator through line 14 passes upward through the ethanolamine solution providing heat to decompose the hydrogen sulfide and carbon dioxide salts and strip them from the ethanolamine solution. A mixture of steam, hydrogen sulfide, and carbon dioxide is then removed overhead from the regenerator through line 16.

As pointed out previously, the feed gases introduced to the system in addition to hydrogen sulfide and carbon dioxide contain various acids and acidic gases which react with the ethanolamine to form heat stable ethanolamine salts. These salts being unaffected by the steam introduced to regenerator 12 pass along with the alkanolamine solution from the bottom of the regenerator through line 18.

An alkali metal hydroxide solution, in this instance, sodium hydroxide having a concentration in the range of about 5 weight percent to about 30 weight percent and preferably in the range from about 10 weight percent to 20 weight percent is combined with the alkanolamine solution through line 20. The sodium hydroxide reacts with the anions of the alkanolamine salts thereby releasing the alkanolamine and forming sodium salts of these anions. The alkanolamine solution containing sodium salts passes through line 22 into a cooler 24 where the solution is reduced in temperature to between about 90° F. and about 105° F. to protect the ion exchange material contained in exchangers 26 and 30. After cooling, the mixture is introduced to anion exchanger 26 which contains a basic anionic exchange resin. In the anion exchanger, hydroxide ion attached to the cationic sites on the resin is displaced by the various anions contained in the sodium salts. The ethanolamine solution then leaves the anion exchanger and passes to the cation exchanger through line 28. In the cation exchanger which contains an acidic cationic resin, hydrogen ions at the anionic sites on the resin are displaced by sodium ions. The hydrogen ions then combine with the hydroxide ions already contained in the amine solution to form water. The ethanolamine solution is now free of sodium salts and can be recycled to the gas treating system through line 32.

Sodium ions are removed from the ethanolamine solution to maintain the heat stable salt anion removal capability in the anion exchanger. If sodium is allowed to remain in solution, hydroxide ions which are exchanged for other anions will also remain in solution. Hydroxide ions then will react with dissolved hydrogen sulfide or carbon dioxide to form bisulfide or bicarbonate ions which will be associated with the sodium ions in solution. These anions will then displace the hydroxide ions on the anion exchange resin and take up sites which are needed for non-regenerable salt anion removal. Replacing the sodium ions with hydrogen ions allows the hydrogen and hydroxide ions to react to form water.

Figure 2:
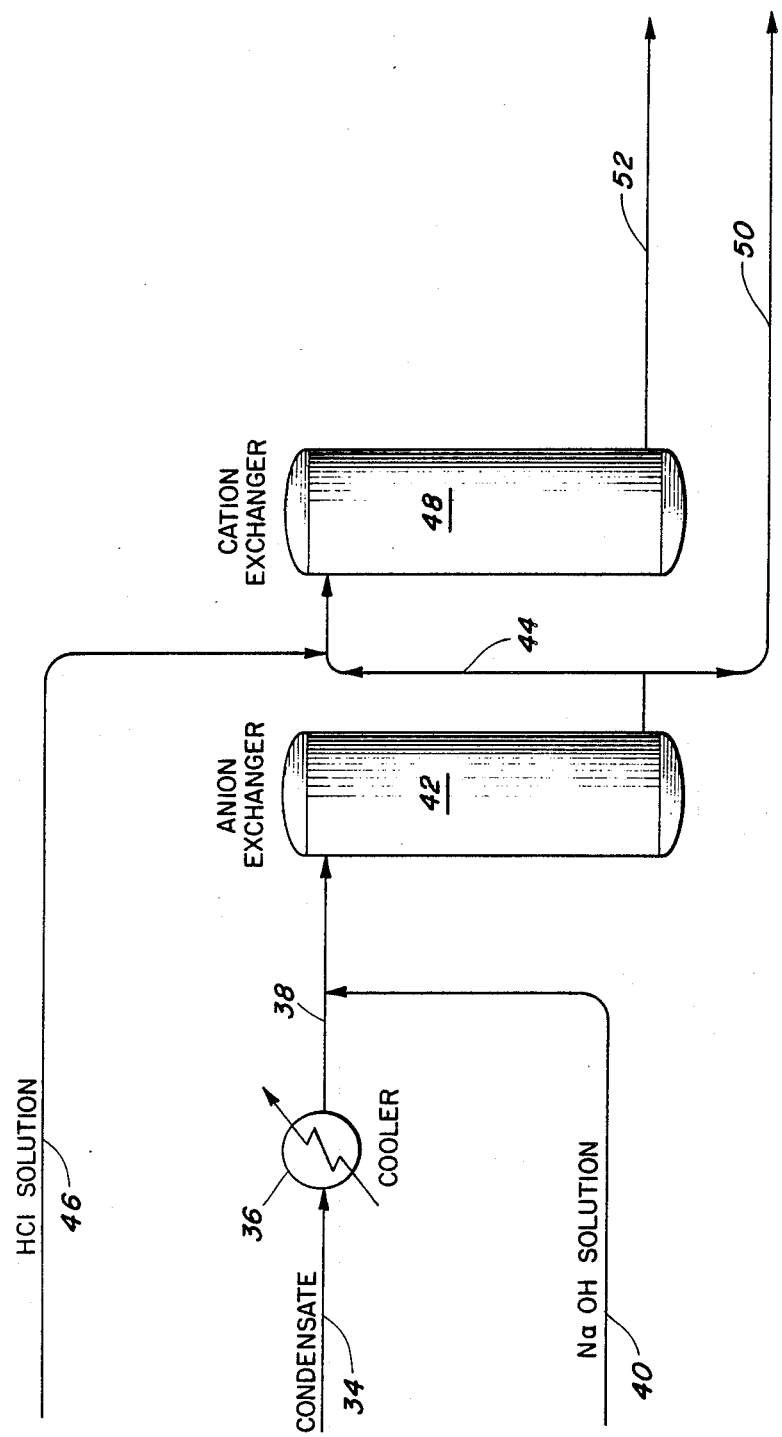
FIG. 2 is a schematic flow diagram which illustrates regeneration of the anion and cation exchange resins.

Periodically, the exchange resins will require regeneration, a procedure for which is illustrated in FIG. 2. To initiate regeneration the flow of amine solution to the exchangers is halted and condensate is introduced to the system through line 34. In order to protect the ion exchange materials, the condensate is cooled in cooler 36 and introduced through line 38 to anion exchanger 42. From there the condensate is passed to cation exchanger 48 and is removed from the unit through line 52. The purpose of the condensate is to flush the exchangers of all ethanolamine. If desired, the condensate containing alkanolamine may be combined with the ethanolamine stream leaving regenerator 12. After the ethanolamine is flushed from the ion exchange resin beds, the two beds are switched from series flow to parallel flow. The anion exchanger is then eluted with a sodium hydroxide stream containing from about 3 to about 6 weight percent sodium hydroxide which is introduced to anion exchanger 42 through lines 40 and 38, and exits the exchanger via line 50. Introduction of the sodium hydroxide is continued until the heat stable salt anions in the anion exchanger have been replaced with hydroxide ions. The cation exchanger 48 is eluted with a hydrochloric acid solution containing from about 3 to about 6 weight percent HCl which is introduced to this exchanger through line 46 and exits therefrom through line 52. Flow of the HCl solution is continued until the sodium ions in the ion exchange resin have been replaced with hydrogen ions. The two streams exiting the exchangers through lines 50 and 52 are normally sent to waste water treating. After elution the two beds are washed with condensate in accordance with the scheme shown in FIG. 3. Condensate provided via line 34, is cooled in cooler 36 and introduced to anionic exchanger 42 through line 38 and cation exchanger 48 through line 54. The condensate exits from the exchangers through lines 56 and 58, respectively. Flow of cooled condensate through the exchangers is continued until the exchangers are free of remaining acid and caustic. The exchangers are then backwashed in parallel flow by introducing condensate to the bottom of exchanger 42 through lines 60 and 56 and into the bottom of exchanger 48 through lines 62 and 58. The condensate backflows through the two exchangers exiting through lines 38 and 54, respectively. The combined condensate streams can then be removed from the unit through line 64. After completion of backwashing the beds may be returned to series flow and the introduction of ethanolamine resumed as illustrated in FIG. 1.

The ion exchange treating system described herein can be used to remove heat stable salts of alkanolamines as well as sodium salts of heat stable salt anions. The heat stable salts may be present due to incomplete reaction of the sodium hydroxide with such salts or they maybe contained in waste amine solutions which also require treatment to recover the amine for further use. Waste amines are generated from purging the circulating system, amine collected from upsets in the circulating system or other contaminated amines. Removing the heat stable salts and sodium salts of heat stable salt anions reduces foaming losses, corrosion, and maximizes the active alkanolamine concentration. Heat stable salt removal from waste amine solutions allows the active amine in the waste solutions to reenter the circulating amine solution without causing additional foaming, corrosion or amine deactivation problems. Also the cost of makeup amine is reduced by returning the waste amine to service in the system.

A variety of basic and acidic ion exchange resins may be used in the process of the invention. Included are such materials as Mobay M500, a strong base anion exchange resin, which is a polystyrene resin with quaternary ammonium groups attached to the polymer framework; Rohm and Haas Amberlyst A-26, a strong base anion exchange resin, which is a styrene/divinyl benzene copolymer with quaternary ammonium groups attached to the polymer framework; Rohm and Haas Amberlite IRC-50, a weak acid cation exchange resin, which is a methacrylic acid/divinyl benzene copolymer with carboxylic acid functional groups attached to the polymer framework; Rohm and Haas Amberlyst A-15, a strong acid cation exchange resin, which is a styrene/divinyl benzene copolymer resin with sulfonic acid groups attached to the polymer framework; and Rohm and Haas Amberlite IR-120, a strong acid cation exchange resin, which is a sulfonic styrene-divinyl benzene copolymer and Rohm and Haas Amberlite IRA-410, a strong base amine-type anion exchange resin. Also included are Dow styrene-divinyl benzene strong base anion exchange resins having quaternary amines as their functional group. These materials are available under the DOWEX trademark.

The following example is presented in illustration of the invention.

EXAMPLE

A sample of methyl diethanolamine gas treating solvent was taken from a refinery gas treating system. The solution was circulated through a conventional absorption column—reboiled regeneration type plant. The solution was in the regenerated form essentially being free of hydrogen sulfide and carbon dioxide. The solution was mechanically filtered through a cotton sock-type cartridge filter vessel, and any remaining hydrocarbons were removed by passing the solution over an activated charcoal bed.

The composition of the solution was determined by analysis to be:

|  | Wt. % |
| --- | --- |
| Free methyldiethanol amine | 38.0 |
| Sodium ion ($Na^+$) | 1.1 |
| Thiocynate ion ($SCN^-$) | 0.83 |
| Other acid gas conjugate base ($A^-$) | 0.24 |

Where the solution medium was water. The symbol "$A^-$" is used to denote anions formed from the reaction of an acid gas with water as shown by:

$$HA_{(g)} + H_2O \rightleftharpoons H_3O^+{}_{(aq)} + A^-{}_{(aq)}$$

The solution from the plant was run through a two stage ion exchange consisting of an anion exchange resin bed and a cation exchange resin bed in series. The anion exchange resin used was Rohm and Haas Amberlyst A-26, a styrene/divinyl benzene copolymer with quaternary ammonium groups attached to the polymer framework. This resin is commonly referred to as strong base anion exchange resin. The cation exchange resin used was Rohm and Haas Amberlite IRC-50, a weak cation exchange resin. The IRC-50 resin is a methacrylic acid/divinyl benzene copolymer with carboxylic acid functional groups attached to the polymer framework. In the test conducted, a two inch diameter anion exchange column was filled to a depth of 16 inches with the anion exchange resin. A two inch diameter cation exchange column was filled to a depth of 11 inches with the cation exchange resins. The anion exchange column was conditioned by running a 5% NaOH regenerant solution over the resin to change it to the hydroxide from the chloride form. The resin was then exhausted by the methydiethanolamine solution. After exhaustion, the bed was again regenerated by a 5% NaOH solution. The exhaustion and regeneration was repeated to establish an equilibrium condition in the resin.

The cation exchanger was prepared by converting it from the sodium form to the hydrogen form by regenerating the resin with a 6% HCl solution. Effluent methyldiethanol amine solution from the anion exchanger was passed over the cation exchange resin until exhaustion. The resin was regenerated with the 6% HCl solution again, and this procedure was repeated until equilibrium conditions were established.

When equilibrium conditions were established, the contaminated amine solution was treated as described in the following discussion.

Methyldiethanolamine solution was passed downward through the anion exchanger bed at a flow of 140 ml/min. The effluent from the anion exchange column was then passed downward through the cation exchanger. The solution was sampled at the outlet of the anion exchanger and at the outlet of the cation exchanger and these samples were analyzed. Samples were taken until both columns were exhausted. Table 1 shows thiocyanate concentrations at various volumes of solution over the anion resin typically achieved in the tests. Table 2 shows sodium concentrations at various volumes passed over the cation resin typically achieved during the tests.

The anion exchange resins were regenerated by passing 750 ml of a 5 wt.% solution of NaOH upward through the resin. After regeneration, the resin was rinsed with 1,000 ml of deionized water downflow through the bed. The cation exchange resins were regenerated by passing 2,750 ml of a 6 wt.% solution of HCl downward through the resin. The resin was then washed with 1,000 ml of deionized water downflow through the resin.

Anion exchanger capacity was computed to be 7.9 Kg equiv./cu.ft. for the A-26 resin. Cation exchanger loading was computed at 52.8 equiv./cu.ft. for the IRC-50 resin.

TABLE 1

| Total Volume MDEA Solution, Liters | Wt. % $SCN^-$ in Effluent |
| --- | --- |
| 1.1 | <0.01 |
| 1.85 | 0.09 |
| 2.6 | 0.15 |
| 3.35 | 0.27 |
| 4.1 | 0.5 |

TABLE 2

| Total Volume MDEA Solution, Liters | Wt. % Na+ in Effluent |
|---|---|
| 0.7 | 0.0 |
| 2.6 | 0.0 |
| 3.6 | 0.006 |
| 4.3 | 0.05 |
| 6.0 | 0.25 |

I claim:

1. In a process for treating an aqueous liquid solution of an alkanolamine containing alkali metal salts of acidic anions which form heat stable salts with said alkanolamine, the improvement which comprises contacting said solution with a basic anion exchange resin wherein the heat stable salt anions are removed from the solution and thereafter contacting said solution with an acidic cation exchange resin to remove alkali metal ions from the solution.

2. The process of claim 1 in which the alkanolamine is selected from the group consisting of ethanolamine, diethanolamine, methyldiethanolamine, diisopropanolamine and triethanolamine.

3. The process of claim 2 in which the alkali metal is sodium.

4. The process of claim 3 in which the acidic anions are selected from the group of organic acids, acid gases and acidic anions consisting of $SO_2$, $COS$, $HCN$, $S_2O_3^=$, $SO_4^=$, $SCN^-$, $HCOOH$, $CH_3COOH$ and $Cl^-$.

5. In a process for treating an aqueous solution of an alkanolamine selected from the group consisting of ethanolamine, diethanolamine, methyl diethanolamine, diisopropanolamine and triethanolamine containing alkali metal salts of inorganic acidic anions, which form heat stable salts with said alkanolamine, the improvement which comprises contacting said solution with a basic anion exchange resin whereby the heat stable anions are removed from the solution and thereafter contacting said solution with an acidic cation exchange resin to remove alkali metal ions from the solution.

6. The process of claim 5 in which the alkanolamine is selected from the group consisting of ethanolamine, diethanolamine, methyldiethanolamine, diisopropylamine and triethanolamine.

7. The process of claim 6 in which the alkali metal is sodium.

8. The process of claim 7 in which the inorganic acidic anions are selected from the group of inorganic acid gases and acidic anions consisting of $SO_2$, $COS$, $HCN$, $S_2O_3^=$, $SO_4^=$, $Cl^-$ and $SCN^-$.

9. A process for removing heat stable salts and alkali metal salts of heat stable salt anions from an admixture of circulating alkanolamine solutions and waste alkanol amine solutions which comprises contacting said admixture with a basic anion exchange resin wherein the heat stable anions are removed the admixture and thereafter contacting said admixture with an acidic cation exchange resin to remove alkali metal ions from the admixture.

10. A process for removing salts from an ethanolamine-water solution comprising the steps of:
   (a) filtering said ethanolamine-water solution to remove suspended particulates,
   (b) contacting said filtered ethanolamine-water solution with an anionic ion-exchange resin, and
   (c) contacting said ethanolamine-water solution with a cationic exchange resin.

11. The process of claim 10 wherein said ethanolamine-water solution comprises a solution of water and one or more of the group consisting of monoethanolamine, diethanolamine, triethanolamine, and methyl diethanolamine.

12. The process of claim 11 wherein said anionic ion-exchange resin contains a quaternary ammonium functional group as the active ion constituent.

13. The process of claim 11 wherein said cationic exchange resin comprises one or more of the group consisting of sulfonic acids and carboxylic acid.

14. The process of claim 11 further comprising contacting said filtered ethanolamine-water solution with a cationic ion-exchange resin prior to contacting said filtered ethanolamine-water solution with an anionic ion-exchange resin.

15. The process of claim 10 wherein said ethanolamine-water solution comprises a solution of water and diethanolamine.

16. The process of claim 10 wherein said ethanolamine-water solution comprises a solution of water and triethanolamine.

17. The process of claim 10 wherein said anionic ion-exchange resin contains a quaternary ammonium functional group as the active ion constituent.

18. The process of claim 10 wherein said cationic exchange resin comprises sulfonic or carboxylic acid or a mixture thereof.

19. The process of claim 10 wherein said anionic and said cationic ion-exchange resins are placed in separate vessels.

20. The process of claim 10 further comprising contacting said filtered ethanolamine-water solution with an anionic ion-exchange resin prior to contacting said filtered ethanolamine-water solution with a cationic ion-exchange resin.

* * * * *